(12) United States Patent
Uno et al.

(10) Patent No.: US 9,347,803 B2
(45) Date of Patent: May 24, 2016

(54) ABNORMALITY DETECTION SYSTEM AND ABNORMALITY DETECTION METHOD

(71) Applicant: FUJITSU LIMITED, Kawasaki-shi, Kanagawa (JP)

(72) Inventors: Kazushi Uno, Atsugi (JP); Fumio Takei, Isehara (JP); Takeo Kasajima, Machida (JP); Kyoko Tadaki, Atsugi (JP); Minoru Ishinabe, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/694,440

(22) Filed: Apr. 23, 2015

(65) Prior Publication Data

US 2015/0241251 A1    Aug. 27, 2015

Related U.S. Application Data

(63) Continuation of application No. PCT/JP2012/077354, filed on Oct. 23, 2012.

(51) Int. Cl.
   *G01D 5/353*  (2006.01)
   *G01K 11/32*  (2006.01)
   *G01L 1/24*   (2006.01)
   *G01N 21/47*  (2006.01)

(52) U.S. Cl.
   CPC ............ *G01D 5/353* (2013.01); *G01D 5/35358* (2013.01); *G01K 11/32* (2013.01); *G01L 1/24* (2013.01); *G01N 21/47* (2013.01)

(58) Field of Classification Search
   None
   See application file for complete search history.

(56) References Cited

U.S. PATENT DOCUMENTS

| | | | | |
|---|---|---|---|---|
| 4,588,255 | A | * | 5/1986 | Tur .................... G06E 3/001 385/24 |
| 5,642,445 | A | * | 6/1997 | Bucaro .............. G01H 3/12 181/125 |
| 5,731,869 | A | | 3/1998 | Minami |
| 6,244,106 | B1 | | 6/2001 | Nakura et al. |

(Continued)

FOREIGN PATENT DOCUMENTS

| | | |
|---|---|---|
| EP | 2 068 126 A1 | 6/2009 |
| EP | 2 120 028 A1 | 11/2009 |

(Continued)

OTHER PUBLICATIONS

International Search Report mailed Dec. 4, 2012 in corresponding international application PCT/JP2012/077354.

(Continued)

*Primary Examiner* — Gordon J Stock, Jr.
(74) *Attorney, Agent, or Firm* — Staas & Halsey LLP

(57) ABSTRACT

An abnormality detection system includes an optical fiber, a backscattered light detection unit, and a data processing unit. The detection unit is connected to one end and the other end of the optical fiber and configured to acquire a first intensity distribution of backscattered light by causing light to enter the optical fiber from the one end, and to acquire a second intensity distribution of backscattered light by causing light to enter the optical fiber from the other end. The processing unit is configured to calculate the product of a value obtained by applying a first FIR filter to the first intensity distribution, and a value obtained by applying a second FIR filter to the second intensity distribution, for each of locations on the optical fiber in the length direction thereof, and to determine whether or not abnormality is present based on the result of the calculation.

20 Claims, 17 Drawing Sheets

(56) References Cited

U.S. PATENT DOCUMENTS

| | | | |
|---|---|---|---|
| 2012/0033709 A1 | 2/2012 | Kasajima et al. | |
| 2013/0202287 A1* | 8/2013 | Joffe | G01M 11/3118 398/13 |
| 2013/0215930 A1 | 8/2013 | Kasajima et al. | |
| 2015/0120194 A1* | 4/2015 | Chen | E21B 47/00 702/6 |
| 2015/0226679 A1* | 8/2015 | Uno | G01K 11/32 702/182 |
| 2015/0233771 A1* | 8/2015 | Uno | G01K 11/3206 374/4 |

FOREIGN PATENT DOCUMENTS

| | | |
|---|---|---|
| JP | 02-123304 | 5/1990 |
| JP | 04-332835 | 11/1992 |
| JP | 7-55332 | 3/1995 |
| JP | 09-18428 | 1/1997 |
| JP | 2584478 | 2/1997 |
| JP | 09-304536 | 11/1997 |
| JP | 10-117424 | 5/1998 |
| JP | 11-183290 | 7/1999 |
| JP | 2011-232138 | 11/2011 |
| WO | WO 2004/104536 A1 | 12/2004 |
| WO | WO 2006/027613 A2 | 3/2006 |
| WO | WO 2010/125712 A1 | 11/2010 |
| WO | WO 2012/056567 A1 | 5/2012 |

OTHER PUBLICATIONS

Extended European Search Report dated Oct. 15, 2015 in corresponding European Patent Application No. 12887297.5.

* cited by examiner

| TIME | LOCATION (m) | LOSS BY PEAK (dB) | LOSS BY LINEAR APPROXIMATION (dB) | ACCURACY (%) |
|---|---|---|---|---|
| 2012/5/20 23:30 | 1353.2 | 0.092 | | |
| 2012/8/20 14:31 | 1847.8 | 0.125 | | |
| 2012/8/22 8:16 | 2027.2 | 0.050 | 0.021 | 99.339 |

| PEAK | LOCATION (m) | PEAK VALUE | AVERAGE LOSS (dB) |
|---|---|---|---|
| P1 | 72.4 | 1132 | 0.01770289 |
| P2 | 77.4 | 18669 | 0.08933878 |
| P3 | 1353.2 | 1586.4 | 0.02729412 |
| P4 | 1847.8 | 2084.5 | 0.0309539 |
| P5 | 2027.2 | 1112.6 | 0.00225068 |
| P6 | 2045.9 | 5115.9 | 0.04637599 |
| P7 | 2050.9 | 1409.2 | 0.01596674 |

FIG.20

| PEAK | LOCATION (m) | PEAK VALUE (dB) | AVERAGE LOSS (dB) |
|---|---|---|---|
| P1 | 72.4 | 0.052 | 0.078 |
| P2 | 77.4 | 0.397 | 0.406 |
| P3 | 1353.2 | 0.092 | 0.120 |
| P4 | 1847.8 | 0.125 | 0.137 |
| P5 | 2027.2 | 0.050 | 0.010 |
| P6 | 2045.9 | 0.234 | 0.206 |
| P7 | 2050.9 | 0.078 | 0.070 |

FIG.21

| PEAK | LOCATION OF LEFT HALF OF FULL WIDTH AT HALF MAXIMUM (m) | LOCATION OF RIGHT HALF OF FULL WIDTH AT HALF MAXIMUM (m) | LF(m) | LR(m) |
|---|---|---|---|---|
| P4 | 1847 | 1848.1 | 1846 | 1849.1 |
| P5 | 2026.5 | 2027.4 | 2025.5 | 2028.4 |
| P6 | 2045.1 | 2046.2 | 2044.1 | 2047.2 |
| P7 | 2050.3 | 2051.3 | 2049.3 | 2052.3 |

| PEAK | LOCATION (m) | LOSS BY LINEAR APPROXIMATION (dB) | AVERAGE LOSS (dB) |
|---|---|---|---|
| P5 | 2027.2 | 0.021 | 0.010 |
| P6 | 2045.9 | 0.219 | 0.206 |

ABNORMALITY DETECTION SYSTEM AND ABNORMALITY DETECTION METHOD

CROSS-REFERENCE TO RELATED APPLICATION

This application is a continuation of International Patent Application No. PCT/JP2012/077354 filed on Oct. 23, 2012 and designated the U.S., the entire contents of which are incorporated herein by reference.

FIELD

The embodiments discussed herein are related to an abnormality detection system and an abnormality detection method.

BACKGROUND

In facilities such as chemical plants, oil refinery plants, and thermal power plants which use large amounts of flammable, explosive, or hazardous materials, it is important to detect corrosion and thinning on pipes and tanks at early stages to prevent serious accidents.

To do so, an abnormality detection system is sometimes employed which includes a temperature distribution measurement apparatus (distributed temperature sensor: DTS) configured to use an optical fiber as a temperature sensor.

This type of abnormality detection system has an optical fiber laid around a pipe or tank, for example, and the optical fiber's end is connected to the temperature distribution measurement apparatus. Then, laser is applied into the optical fiber from the temperature distribution measurement apparatus, and Raman scattered light generated inside the optical fiber is detected with the temperature distribution measurement apparatus to acquire the temperature of the pipe or tank, and the presence of abnormality is determined based on the obtained result.

In facilities such as chemical plants, oil refinery plants, and thermal power plants, a delay in abnormality detection may lead to serious accidents. Thus, a system capable of detecting the occurrence of abnormality at an even earlier stage is desired.

Note that the following patent documents disclose a technique related to the present application.

Patent Document 1: Japanese Laid-open Patent Publication No. 09-18428
Patent Document 1: Japanese Laid-open Patent Publication No. 02-123304
Patent Document 3: International Patent Pamphlet No. WO 2010/125712

SUMMARY

According to one aspect of a technique disclosed herein, there is provided an abnormality detection system, including: an optical fiber; a backscattered light detection unit connected to one end and another end of the optical fiber and configured to acquire a first intensity distribution of backscattered light by causing light to enter the optical fiber from the one end, and to acquire a second intensity distribution of backscattered light by causing light to enter the optical fiber from the other end; and a data processing unit configured to calculate a product of a value obtained by applying a first FIR (Finite Impulse Response) filter to the first intensity distribution acquired by the backscattered light detection unit, and a value obtained by applying a second FIR filter to the second intensity distribution acquired by the backscattered light detection unit, for each of locations on the optical fiber in a length direction of the optical fiber, and to determine whether or not abnormality is present based on a result of the calculation.

According to another aspect of the disclosed technique, there is provided an abnormality detection method, including: by using a backscattered light detection unit, acquiring a first intensity distribution of backscattered light by causing light to enter an optical fiber from one end of the optical fiber, and, by using the backscattered light detection unit, acquiring a second intensity distribution of backscattered light by causing light to enter the optical fiber from another end of the optical fiber; and by using a data processing unit, calculating a product of a value obtained by applying a first FIR (Finite Impulse Response) filter to the first intensity distribution, and a value obtained by applying a second FIR filter to the second intensity distribution for each of locations on the optical fiber in a length direction of the optical fiber.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 20 is a table illustrating the result of finding average losses by using the correction function $F(\Delta P)$;

FIG. 21 is a table illustrating the locations of the full width at half maximum of each of peaks P4 to P7, and locations LF and LR;

DESCRIPTION OF EMBODIMENTS

Before describing an embodiment, a prelude for facilitating understanding of the embodiment will be described below.

An abnormality detection system according to the embodiment detects abnormality by utilizing the fact that the transmission loss of an optical fiber changes in response to application of bending stress.

Figure 1:
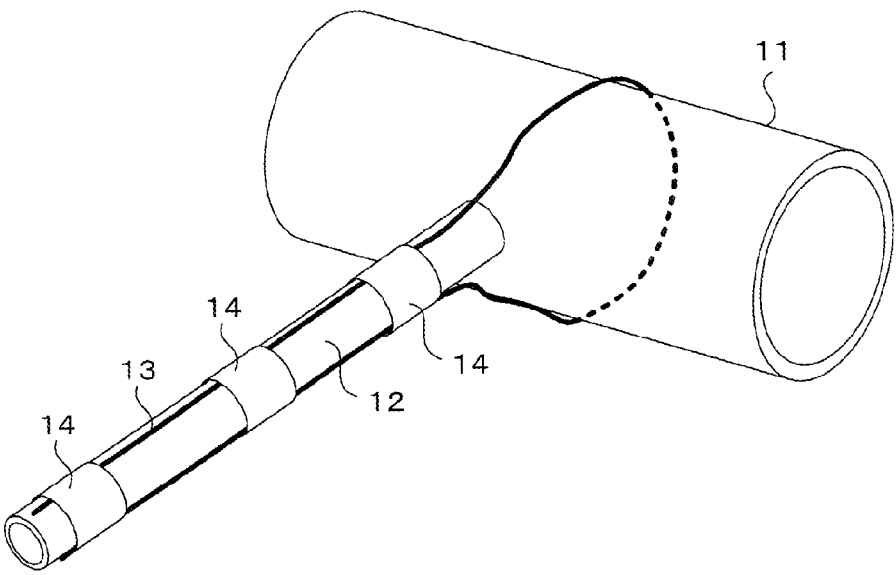
FIG. 1 is a view illustrating a state where an optical fiber is wound with a constant tension around a portion of a main pipe where a branch pipe is welded.

FIG. 1 is a view illustrating a state where an optical fiber 13 is wound with a constant tension around a portion of a main pipe 11 where a branch pipe 12 is welded. The optical fiber 13 is partly fixed to the branch pipe 12 with pieces of tape 14.

The flow of liquid or gas inside the main pipe 11 and the branch pipe 12 changes as the plant is operated and stopped. As a result, the temperature of the main pipe 11 and the branch pipe 12 changes accordingly. By this temperature change, the main pipe 11 and the branch pipe 12 expand or shrink, and the bending stress and the tensile stress applied to the optical fiber 13 change accordingly.

When the optical fiber 13 receives a bending stress or tensile stress of a certain degree or higher, the transmission loss thereof increases. It is, then, possible to determine the presence of abnormality, for example, by comparing the transmission loss in a past operating or stopped period and the current transmission loss.

Figure 2:
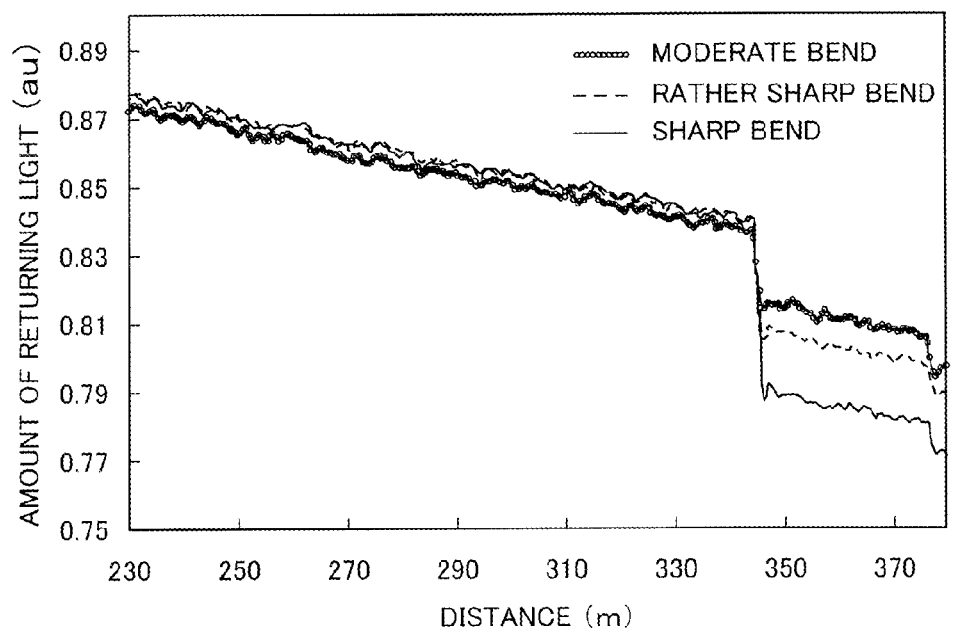
FIG. 2 is a graph illustrating the results of observation on transmission loss in a state where the optical fiber is bent moderately, transmission loss in a state where the optical fiber is bent rather sharply, and transmission loss in a state where the optical fiber is bent sharply.

FIG. 2 is a graph with the horizontal axis representing distance (location of the optical fiber in the length direction thereof) versus the vertical axis representing the intensity of returning light, illustrating the results of observation on the transmission loss in a state where the optical fiber is bent moderately, the transmission loss in a state where the optical fiber is bent rather sharply, and the transmission loss in a state where the optical fiber is bent sharply.

Figure 3:
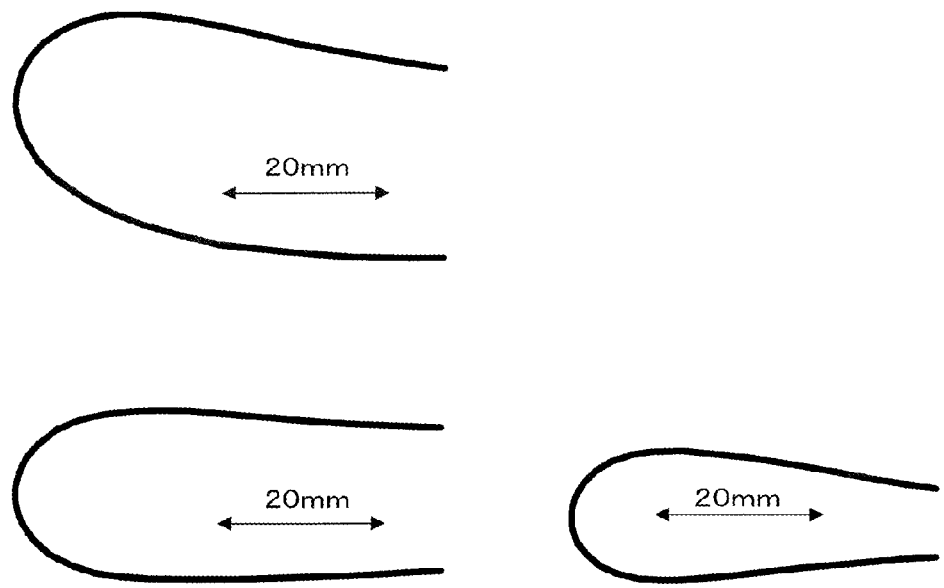
FIG. 3 is a view specifically illustrating the moderate bend, the rather sharp bend, and the sharp bend.

Note that the moderate bend refers to a bend (with a bend radius of about 10 mm) as illustrated in FIG. 3; the rather sharp bend refers to a bend slightly sharper than that of the moderate bend (see FIG. 3); and the sharp bend refers to a bend slightly sharper than that of the rather sharp bend (see FIG. 3). Moreover, in FIG. 2, the intensity of returning light is normalized based on the amount of light at a 0-m location in the optical fiber in the length direction.

FIG. 2 indicates that transmission losses occur at an approximately 340-m location in the optical fibers in the length direction in accordance with the degrees of the bends.

Assume for example that, during normal operation, an optical fiber is bent moderately and a certain amount of transmission loss occurs at a given location in the optical fiber in the length direction. In this case, it is possible to determine that some abnormality has occurred if the transmission loss of the optical fiber abruptly changes.

As indicated by FIG. 2, the intensity of returning light changes by the location in the optical fiber in the length direction. It is therefore impossible to determine the presence of abnormality simply from the intensity of returning light. Hence, in order to automatically detect abnormality, it is important to detect change in the intensity of returning light.

Patent Document 1 describes a method in which the intensity distribution of returning light is differentiated twice for the purpose of accurately measuring the location of a connected portion of optical fibers and the connection loss thereat. It is conceivable to utilize this method to detect the presence of abnormality.

Figure 4:
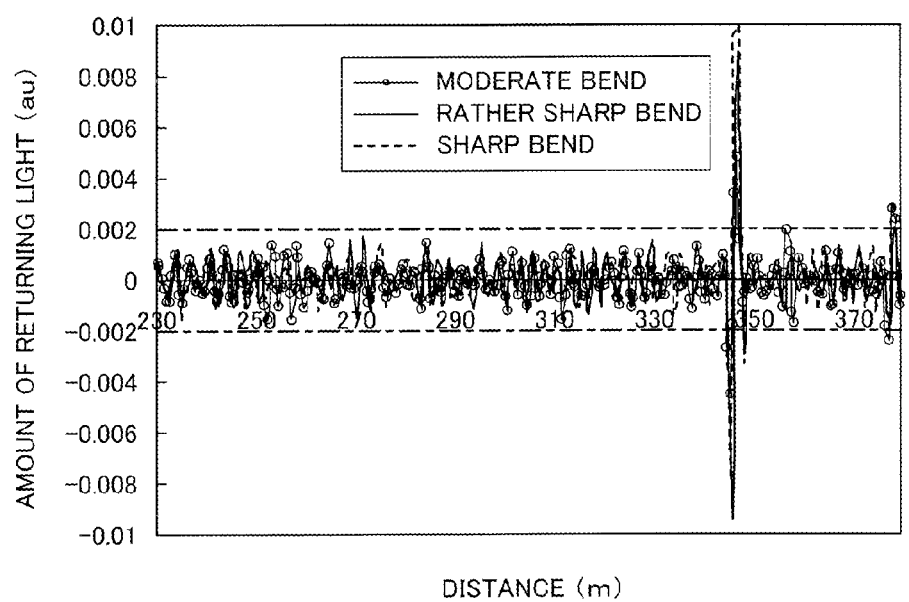
FIG. 4 is a graph illustrating the result of double differentiation on the intensity distributions of returning light illustrated in FIG. 2.

FIG. 4 is a graph illustrating the result of double differentiation on the intensity distributions of returning light illustrated in FIG. 2. The dashed lines in FIG. 4 indicate a range of $3\sigma$ ($\sigma$ is the standard deviation).

As illustrated in this FIG. 4, the double differentiation on the intensity distributions of returning light heightens the changes in the intensities of the returning light. It is thus possible to relatively accurately detect the presence of a transmission loss and the location where the transmission loss has occurred.

Here, it is preferable to set a threshold to about $3\sigma$ in order to remove noise components. In the case where the threshold is set at $3\sigma$, the reliability of the detection is not said to be high since the peak level at the moderately bent portion is slightly higher than the noise level.

FIG. 2 indicates that the difference between the amounts of returning light before and after the rather sharply bent location is approximately 2.4%. In other words, this method does not accurately detect the occurrence of abnormality unless there is a bending stress or tensile stress that changes the amount of light by at least 2.4%.

While an optical pulse detector (Optical Time Domain Reflectmeter: OTDR) used in Patent Document 1 uses Rayleigh scattered light, a similar result may be obtained by using Raman scattered light which is used by temperature distribution measurement apparatuses (DTS). By using a temperature distribution measurement apparatus, it is possible to perform temperature distribution measurement and abnormality detection at the same time.

Figure 5:
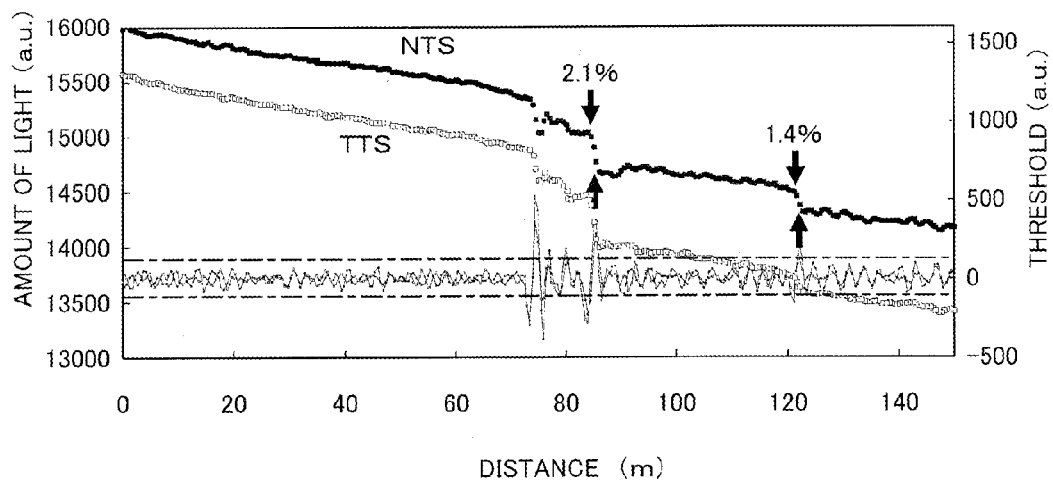
FIG. 5 is a graph illustrating the intensity distribution of Raman scattered light in a state where a bending stress is applied, together with the result of double differentiation on the intensity distribution.

FIG. 5 is a graph with the horizontal axis representing distance (location of the optical fiber in the length direction) versus the vertical axis representing the amount of returning light (left) and threshold (right), illustrating the intensity distribution of Raman scattered light in a state where a bending stress is applied, together with the result of double differentiation on the intensity distribution. Note that in FIG. 5, NTS indicates a measurement result for Stokes light while TTS indicates a measurement result for anti-Stokes light. Moreover, the dashed lines in FIG. 5 indicate a range of 3σ.

This FIG. 5 indicates that, without about a 2%-difference in the amount of light, the method involving double differentiation on returning light does not accurately detect abnormality even by using Stokes light and anti-Stokes light.

Thus, the method of detecting abnormality through double differentiation on the intensity distribution of returning light has this problem in that abnormality is not detected until the transmission loss increases to a certain extent, i.e. abnormality is not detected at an early stage. In facilities such as factories and chemical plants, it is desired to detect abnormality at an early stage because a delay in abnormality detection may worsen accidents.

Another reason for the incapability of detecting abnormality at an early stage is the influence of temperature. The intensity of Raman scattered light changes with temperature. Hence, the intensity of returning light is related to the stress applied to the optical fiber and the temperature.

Figure 6:
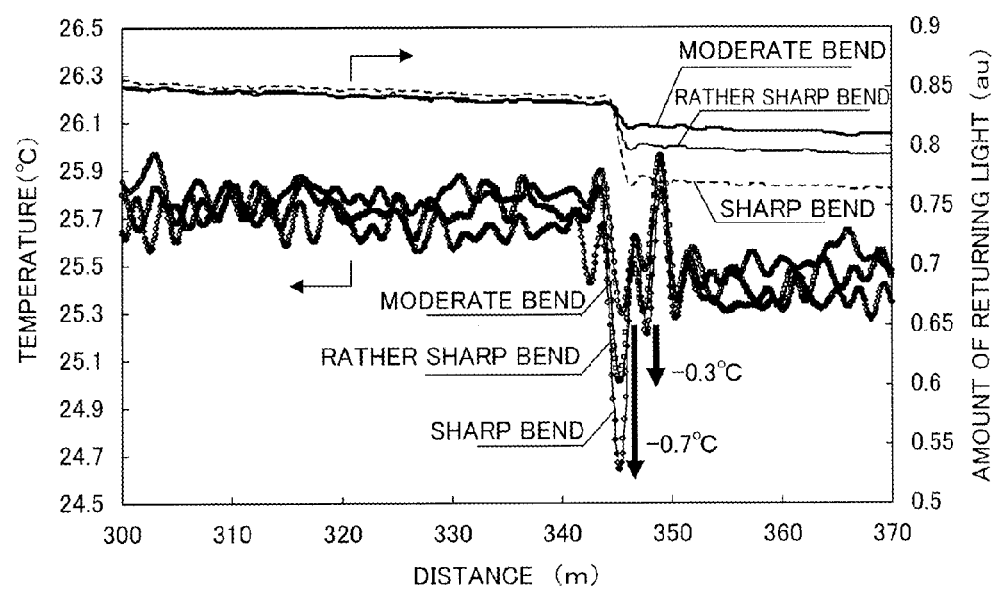
FIG. 6 is a graph illustrating the intensity distributions of returning light together with corresponding temperature distributions obtained by a temperature distribution measurement apparatus.

FIG. 6 is a graph with the horizontal axis representing distance (location of the optical fiber in the length direction) versus the vertical axis representing temperature (left) and the intensity of returning light (right), illustrating the intensity distributions of returning light together with corresponding temperature distributions obtained by a temperature distribution measurement apparatus.

Note that in FIG. 6, the intensity of returning light is normalized based on the amount of light at a 0-m location in the optical fiber in the length direction. Moreover, in this example, a bending stress is applied to an approximately 345-m location on the optical fiber in the length direction.

FIG. 6 indicates that the error in measured temperature is large when the bend radius of the optical fiber is small and the transmission loss is thus large. Note that in FIG. 6, the temperature difference between before and after the location where the bending stress is applied is not a problem since it originates from the positional difference therebetween on the path along which the optical fiber is laid.

There is a case, for example, where a housing-type data center is performing temperature monitoring by using optical fibers, and the stress applied to an optical fiber laid on a rack has changed for some reason, thereby changing the intensity of returning light and making it impossible to accurately detect the temperature. In this case, the temperature is detected to be higher than the actual temperature, or the temperature is detected to be lower than the actual temperature.

In the case where the temperature is detected to be higher than the actual temperature, abnormality is determined to be present although there is no abnormality. On the other hand, in the case where the temperature is detected to be lower than the actual temperature, no abnormality is determined to be present although the temperature is above an allowable upper limit temperature.

In the following embodiment, an abnormality detection system will be described which is capable of detecting abnormality at an early stage, the abnormality occurring in a facility such as a chemical plant, an oil refinery plant, or a thermal power plant.

EMBODIMENT

Figure 7:
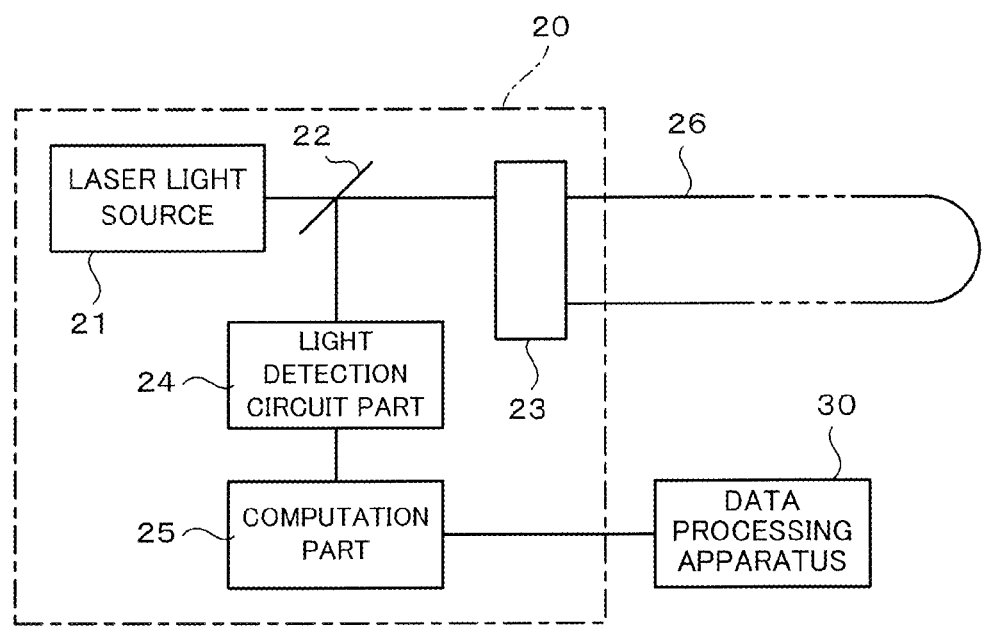
FIG. 7 is a block diagram illustrating an abnormality detection system according to an embodiment.

FIG. 7 is a block diagram illustrating an abnormality detection system according to an embodiment.

The abnormality detection system according to this embodiment includes a loop-type light detection apparatus 20 and a data processing apparatus 30 configured to process data outputted from the light detection apparatus 20. The loop-type light detection apparatus 20 is one example of a backscattered light detection unit, and the data processing apparatus 30 is one example of a data processing unit.

The loop-type light detection apparatus 20 includes a laser light source 21, a beam splitter 22, a transmission path switcher 23, a light detection circuit part 24, and a computation part 25. The loop-type light detection apparatus 20 is used while connected to an optical fiber 26. The optical fiber 26 is connected at both ends to the transmission path switcher 23, and laid on the peripheries of pipes 11 and 12 and partly fixed to the pipes 11 and 12 with pieces of tape 14 or the like as in FIG. 1, for example.

The laser light source 21 is configured to output laser of a predetermined pulse width at regular intervals. This laser travels through the beam splitter 22 and enters the optical fiber 26 through the transmission path switcher 23.

The transmission path switcher 23 is configured to switch the transmission path of the laser at regular intervals. Specifically, the transmission path switcher 23 alternately switches the transmission path between a state where one end of the optical fiber 26 and the beam splitter 22 are optically connected to each other (see FIG. 8A) and a state where the other end of the optical fiber 26 and the beam splitter 22 are optically connected to each other (see FIG. 8B).

Part of the light having entered the optical fiber 26 is backscattered by molecules composing the optical fiber 26. The backscattered light travels backward through the optical fiber 26, passes through the transmission path switcher 23, and reaches the beam splitter 22. The light is then reflected on the beam splitter 22 and reaches the light detection circuit part 24.

The light detection circuit part 24 is provided with a filter (not illustrated) configured to separate the light into light of predetermined wavelengths, and a light receiving element (not illustrated) configured to receive the light of the predetermined wavelengths separated by the filter. Moreover, the light detection circuit part 24 is configured to output a signal corresponding to the intensity of the light received by the light receiving element.

The computation part 25 includes a computer as its constituent component. This computation part 25 is configured to store the time-series changes in the signal outputted from the light detector circuit part 24 and output these pieces of data to the data processing apparatus 30.

The data processing apparatus 30 includes a computer as its constituent component. Moreover, as will be described later, the data processing apparatus 30 is configured to determine the presence of abnormality by processing data outputted from the light detection apparatus 20, and perform a preset process such as putting out an alert if determining that abnormality is present.

As the loop-type light detection apparatus 20, a light pulse detector (OTDR) using Rayleigh scattered light may be used, or a temperature distribution measurement apparatus (DTS) using Raman scattered light (Stokes light and anti-Stokes light) may be used. In the case of using the temperature distribution measurement apparatus as the light detection apparatus 20, it is possible to perform temperature distribution measurement in addition to abnormality detection.

Note that the present inventors have proposed a temperature measurement method in which the temperature at a given measurement point is set as a reference, and the measured temperature values at the other measurement points are corrected using a transfer function (e.g. Patent Document 3). With this method, it is possible to accurately detect the temperature at measurement points set at intervals of 10 cm to several tens of cm in the length direction of the optical fiber.

Figure 9A:
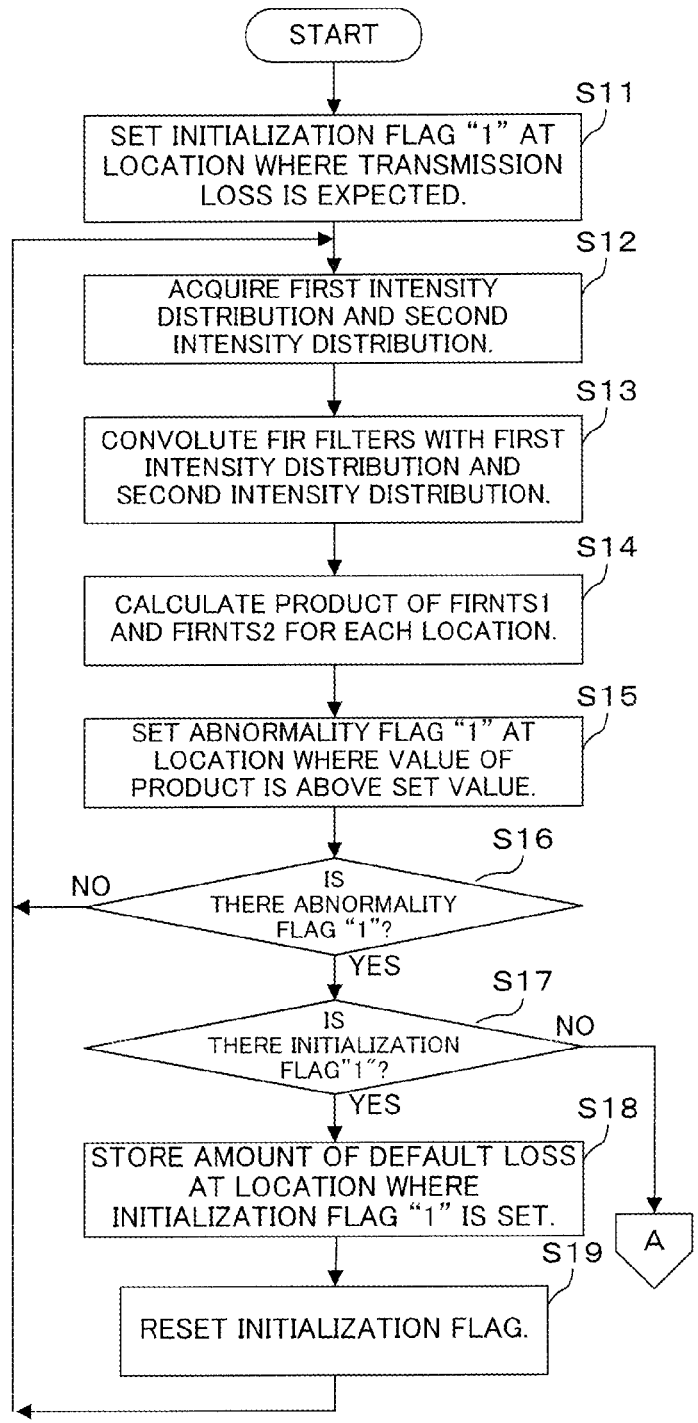
FIGS. 9A and 9B are a flowchart illustrating an abnormality detection method.
Figure 9B:
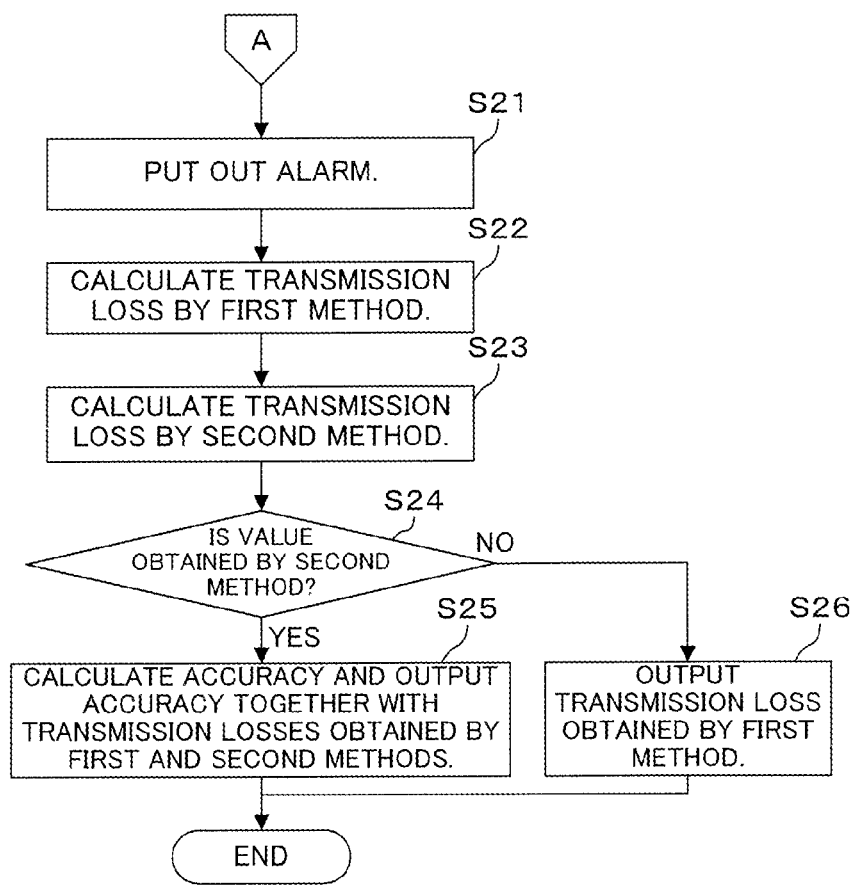

An abnormality detection method of the abnormality detection system according to this embodiment will be described below with reference to a flowchart illustrated in FIGS. 9A and 9B.

First, in step S11, an initialization flag "1" is set at a predetermined location on the optical fiber 26 in the length direction.

For example, in the case two optical fibers 26 are optically connected with a connector or by fusion, a transmission loss inevitably occurs at the connected portion. Thus, even if a transmission loss of a certain degree occurs at the connected portion, it is not a sign of abnormality. In step S11, the initialization flag "1" is set at a location where a transmission loss is expected, like the connected portion. Moreover, in the case where a stress of a certain degree is applied in advance to a particular location on the optical fiber 26, the initialization flag "1" is also set on that location.

Then, in step S12, the data processing apparatus 30 acquires an intensity distribution in the optical fiber 26 in the length direction, which is obtained by applying laser to the optical fiber 26 from the one end (see FIG. 8A), and sets the intensity distribution as a first intensity distribution. Moreover, the data processing apparatus 30 acquires an intensity distribution in the optical fiber 26 in the length direction, which is obtained by applying laser to the optical fiber 26 from the other end (see FIG. 8B), and sets the intensity distribution as a second intensity distribution.

Figure 10:
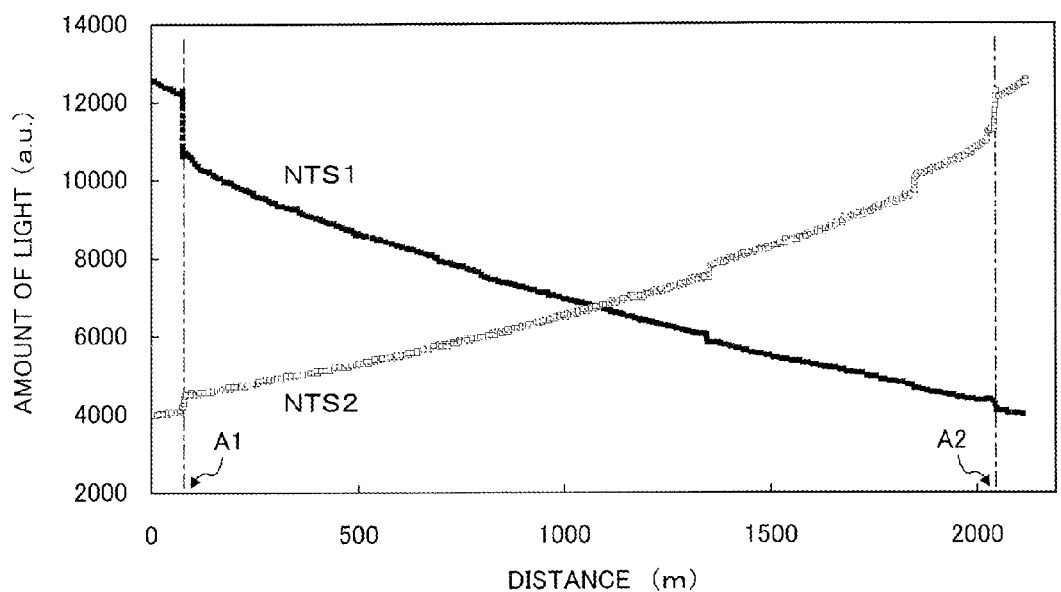
FIG. 10 is a graph illustrating a first intensity distribution (NTS1) and a second intensity distribution (NTS2)

FIG. 10 is a graph with the horizontal axis representing distance (location of the optical fiber 26 in the length direction) versus the vertical axis representing the intensity (amount) of returning light (backscattered light) detected by the light detection apparatus 20, illustrating the first intensity distribution (NTS1) and the second intensity distribution (NTS2).

Figure 8A:
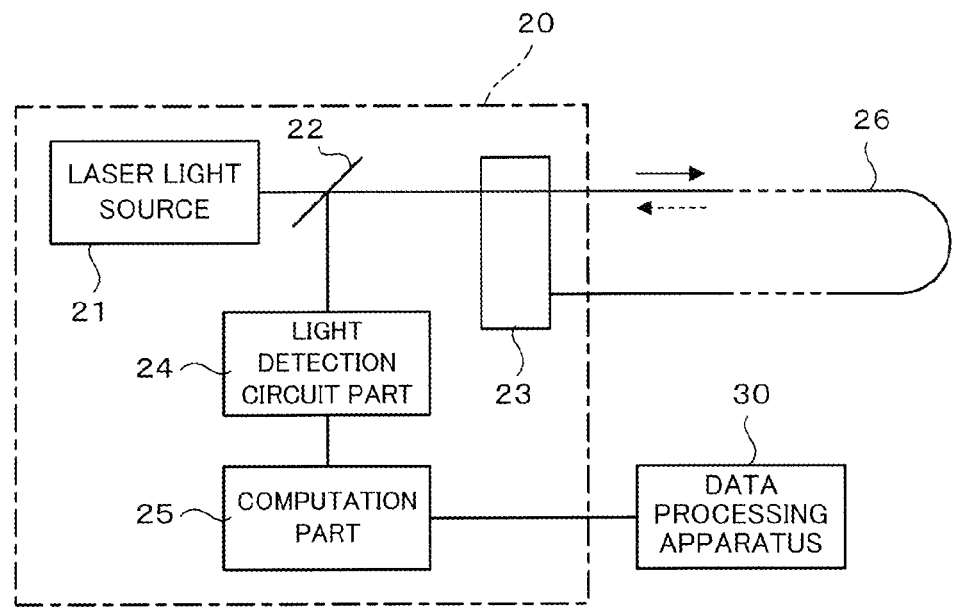
FIG. 8A is a diagram illustrating a state where one end of an optical fiber and a beam splitter are optically connected to each other.

Note that the horizontal axis of FIG. 10 represents the distance from a reference location (0 m) which is a predetermined location on the laser light source 21 side of the optical fiber 26 in the state where the light detection apparatus 20 and the one end of the optical fiber 26 are optically connected to each other as illustrated in FIG. 8A. Moreover, the transmission losses at locations indicated by A1 and A2 in FIG. 10 are losses that have occurred at connectors optically connecting the light detection apparatus 20 to the one end and the other end of the optical fiber 26.

Figure 8B:
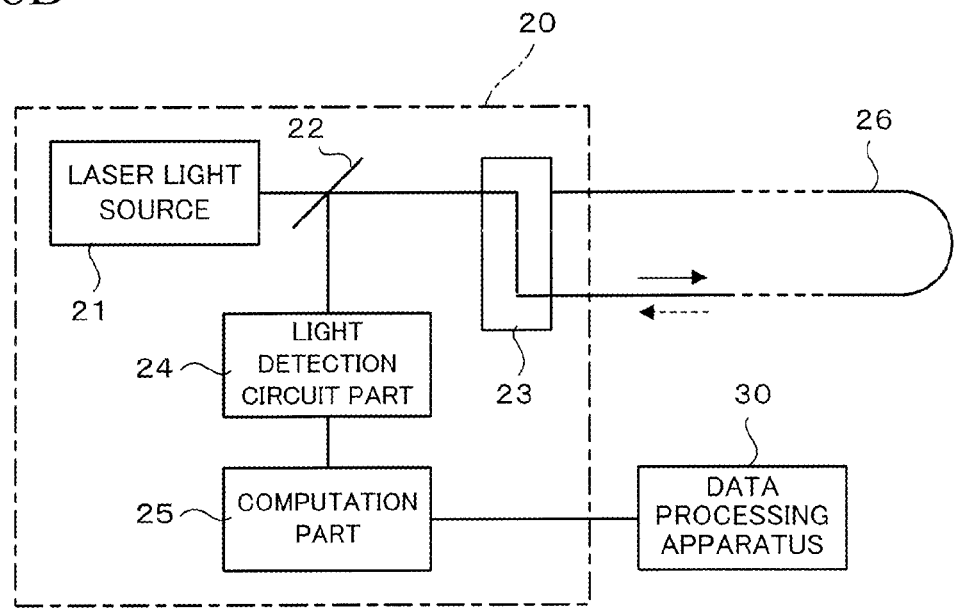
FIG. 8B is a diagram illustrating a state where the other end of the optical fiber and the beam splitter are optically connected to each other.

The intensity distribution (NTS1) of backscattered light resulting from the application of laser to the optical fiber 26 from the one end as illustrated in FIG. 8A is such that the closer it gets to the reference location (0-m location), the higher the backscattered light becomes, and the farther it gets away from the reference location, the lower the backscattered light becomes. Moreover, the intensity distribution (NTS2) of backscattered light resulting from the application of laser to the optical fiber 26 from the other end as illustrated FIG. 8B is such that the closer it gets to the reference location, the lower the backscattered light becomes, and the farther it gets away from the reference location, the higher the backscattered light becomes.

Proceeding then to step S13, the data processing apparatus 30 applies differential FIR (Finite Impulse Response) filters to the first intensity distribution (NTS1) and the second intensity distribution (NTS2), respectively.

Figure 11A:
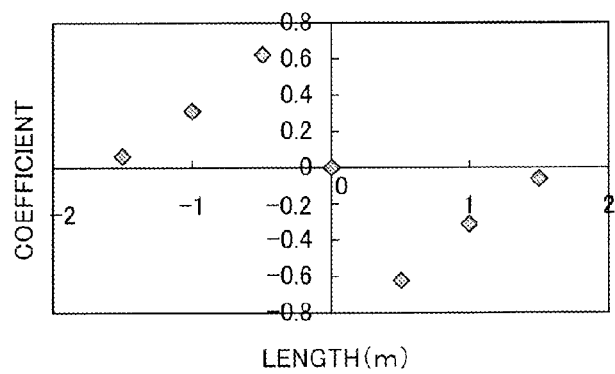
FIGS. 11A and 11B are graphs illustrating one example of FIR filters.
Figure 11B:
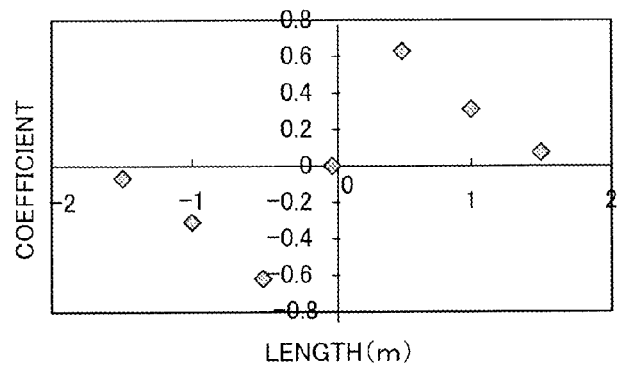

The differential FIR filters are each a filter which has the characteristics of both a differential filter and a low-pass filter, unlike a unit-step-type differential filter. FIGS. 11A and 11B illustrate one example of the FIR filters used in this embodiment.

FIG. 11A illustrates the FIR filter to be used for the application to the first intensity distribution (NTS1) from the reference location side, and FIG. 11B illustrates the FIR filter to be used for the application to the second intensity distribution (NTS2) from the reference location side. The FIR filter in FIG. 11B has characteristics symmetric with the characteristics of the FIR filter in FIG. 11A in positive-negative directions. Note that the FIR filter in FIG. 11A may be used in the case of the application to the second intensity distribution (NTS2) from the opposite side from the reference location.

Figure 12:
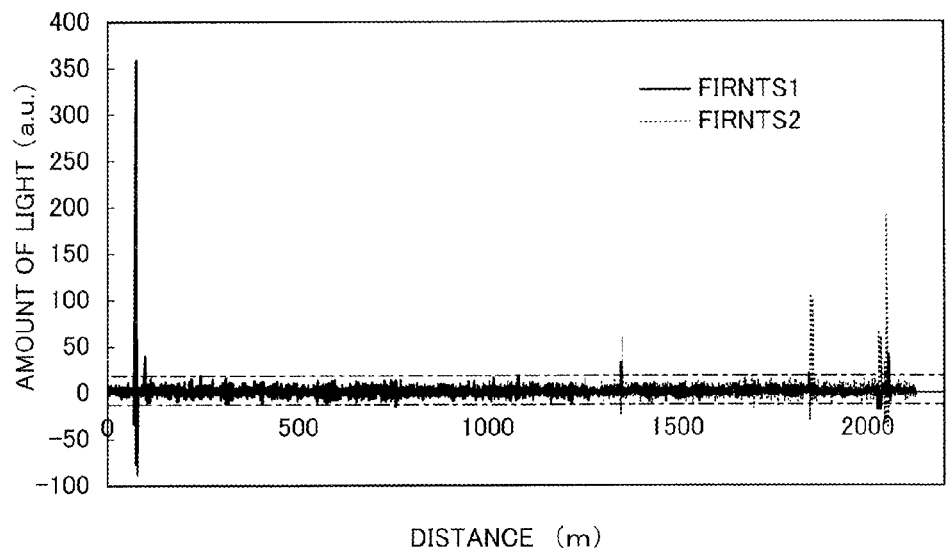
FIG. 12 is a graph illustrating the result of convoluting the FIR filter illustrated in FIG. 11A with the first intensity distribution (NTS1) and the result of convoluting the FIR filter illustrated in FIG. 11B with the second intensity distribution (NTS2)

FIG. 12 is a graph illustrating the result of convoluting the FIR filter illustrated in FIG. 11A with the first intensity distribution (NTS1) and the result of convoluting the FIR filter illustrated in FIG. 11B with the second intensity distribution (NTS2). In FIG. 12, FIRNTS1 represents the result of the convolution of the FIR filter illustrated in FIG. 11A with the first intensity distribution (NTS1), while FIRNTS2 represents the result of the convolution of the FIR filter illustrated in FIG. 11B with the second intensity distribution (NTS2).

As illustrated in this FIG. 12, transmission losses are heightened by convoluting the first FIR filter and the second FIR filter with the first intensity distribution and the second intensity distribution, respectively. Here, the reference location is on the one end side of the optical fiber 26, FIRNTS1 has higher sensitivity on the reference location side while FIRNTS2 has higher sensitivity on the opposite side from the reference location.

Proceeding then to step S14, the data processing apparatus 30 calculates the product of the value of FIRNTS1 and the value of FIRNTS2 for each of given locations L on the optical fiber 26 in the length direction.

Figure 13:
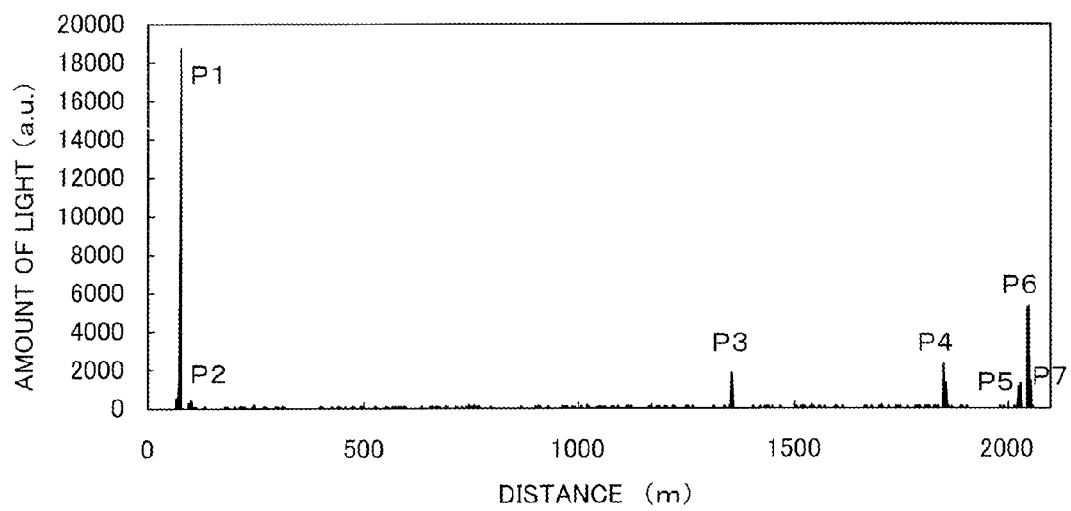
FIG. 13 is a graph obtained by calculating the product of the value of FIRNTS1 and the value of FIRNTS2 for each of given locations on the optical fiber in the length direction thereof.

FIG. 13 is a graph obtained by calculating the product of the value of FIRNTS1 and the value of FIRNTS2 for each of the given locations on the optical fiber 26 in the length direction. Also, FIG. 14A is a graph illustrating the 50-m to 100-m range in FIG. 13 on a larger scale, and FIG. 14B is a graph illustrating the 1800-m to 2100-m range in FIG. 13 on a larger scale.

Figure 14A:
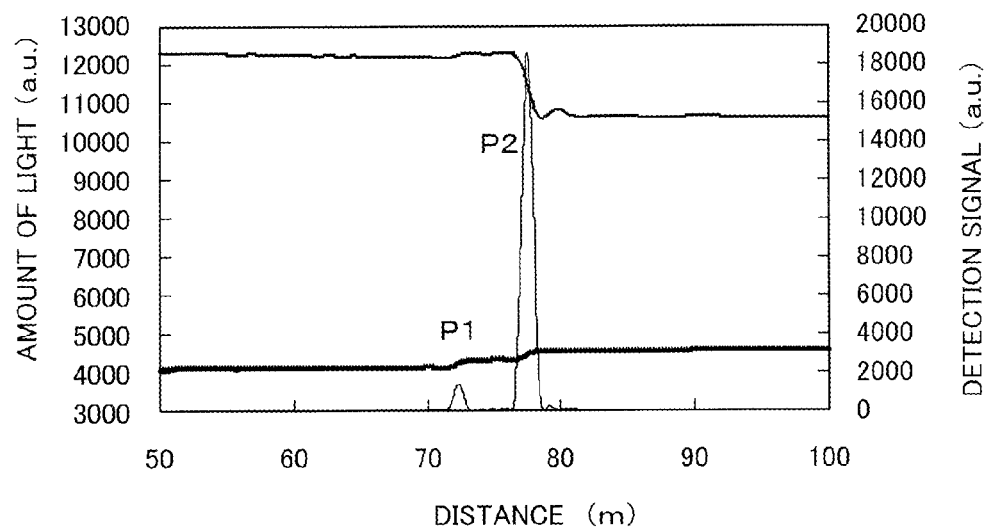
FIGS. 14A and 14B are graphs illustrating sections of FIG. 13 on larger scales.
Figure 14B:
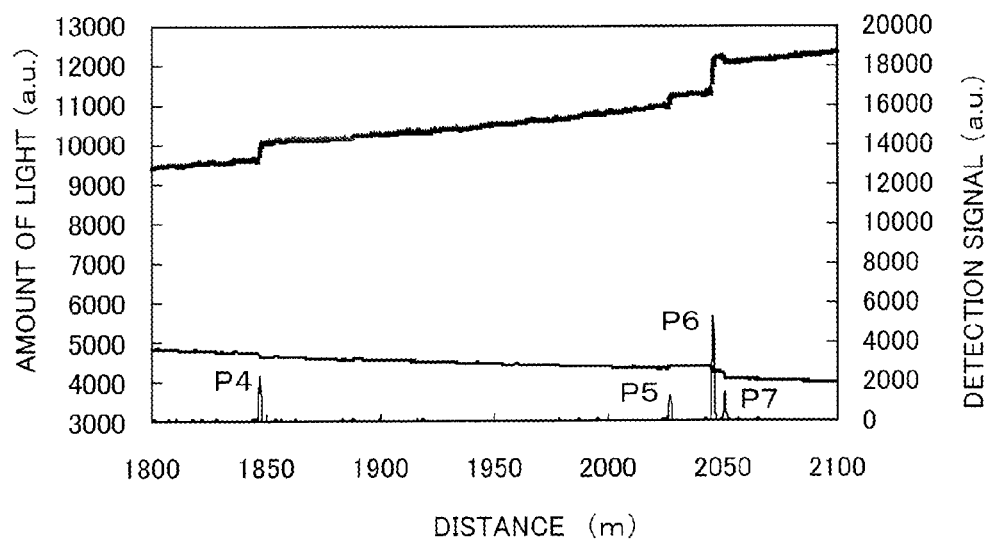

As is clear from these FIGS. 13, 14A and 14B, the computation of the product of the value of FIRNTS1 and the value of FIRNTS2 reduces the noise components and hence further heightens the transmission losses. It may be seen that, in this example, there are seven peaks P1 to P7, and transmission losses have occurred at these locations.

Proceeding then to step S15, the data processing apparatus 30 compares the value of the product of the value of FIRNTS1 and the value of FIRNTS2 with a set value for each location L. If the value of the product of the value of FIRNTS1 and the value of FIRNTS2 is greater than the set value, the data processing apparatus 30 determines that abnormality is present, and sets an abnormality flag "1" at that location L.

The set value may be set to about $3\sigma$, for example. Note that, in the case where a later-described default loss is registered at the location L, the set value is set to (default loss+error range).

Note that a transmission loss above the set value occurs at each of the portions where the initialization flag "1" is set in step S11, i.e. the connected portion of the optical fibers and the portion thereof where a stress of a certain degree is applied in advance. Thus, in the first loop, the abnormality flag "1" is set at each of these portions.

Proceeding then to step S16, the data processing apparatus 30 determines whether or not there is any location where the abnormality flag "1" is set. The data processing apparatus 30 proceeds to step S17 if determining that there is a location where the abnormality flag "1" is set. The data processing apparatus 30 returns to step S12 and continues the process if determining that there is no location where the abnormality flag "1" is set.

If proceeding to step S17 from step S16, the data processing apparatus 30 determines whether or not the initialization flag "1" is set at the location where the abnormality flag "1" is set. The data processing apparatus 30 proceeds to step S18 if determining that the initialization flag "1" is set at the location where the abnormality flag "1" is set. The data processing apparatus 30 proceeds to step S21 if determining that the initialization flag "1" is not set.

If proceeding to step S18 from step S17, the data processing apparatus 30 registers the value of FIRNTS1 and the value of FIRNTS2 at the location L where the initialization flag "1" is set, as a default loss and stores it in the data processing apparatus 30. In the following, the value of FIRNTS1 at the location L will be described as FIRNTS1(L) and the value of FIRNTS2 at the location L will be described as FIRNTS2(L).

Proceeding then to step S19, the data processing apparatus 30 resets the initialization flag "1". Thereafter, the data processing apparatus 30 returns to step S12 and repeats the process described above.

In the second and subsequent loops, the initialization flags have already been reset. Hence, if there is any location where the abnormality flag "1" is set in step S15, the data processing apparatus 30 proceeds to step S21 from step S17.

Once proceeding to step S21, the data processing apparatus 30 notifies the presence of abnormality by putting out an alert, for example. Proceeding then to step S22, the data processing apparatus 30 performs a calculation to quantify the amount of loss by using a first method.

In the first method, data is normalized, and the amount of loss (dB) is found from the height of the corresponding peak from a baseline based on a configuration table. The data processing apparatus 30 calculates the amount of loss from the method described below, for example.

First, the data processing apparatus 30 calculates an abnormality detection signal P(L) for each location from the equation (1) given below.

$$P(L)=FIRNTS1(L) \cdot FIRNTS2(L) \quad (1)$$

The abnormality detection signal P(L) has a peak waveform at the location where abnormality has occurred. With Lalert (L=Lalert) as the location of the peak's maximum height, and Pave as the average of the abnormality detection signal P(L) excluding the peak waveform around Lalert, an effective peak height $\Delta P$ is expressed by the equation (2) given below.

$$\Delta P=P(\text{Lalert})-Pave \quad (2)$$

Here, a transmission loss Loss1(L) is calculated from the equation (3) given below with $F(\Delta P)$ as a correction function.

$$\text{Loss1}(L)=-10 \cdot \log(1-F(\Delta P)) \quad (3)$$

Here, with constants a and b, $F(\Delta P)$ is expressed by the equation (4) given below.

$$F(\Delta P)=a \cdot \ln(\Delta P)-b \quad (4)$$

Once the amount of loss Loss1(L) is found by the first method as described above, the data processing apparatus 30 proceeds to step S23. Then, in step S23, the data processing apparatus 30 attempts to quantify the amount of loss by using a second method.

The second method is under the assumption that a loss spot of interest has other loss spots present on both sides thereof. The other loss spots may each be the location of a neighboring peak or a location where a default loss is registered like the connected portion of optical fibers. Then, the values of the spots before and after the location where abnormality is detected are linearly approximated by the least-median-of-squares (LMedS) method or the like, and the loss (dB) is found from the difference between these segments.

In this case, too, like the first method, an abnormality detection signal P(L) is calculated for each location from the equation (5) given below.

$$P(L)=FIRNTS1(L) \cdot FIRNTS2(L) \quad (5)$$

The abnormality detection signal P(L) has a peak waveform at the location where abnormality has occurred. With Lalert (L=Lalert) as the location of the peak's maximum height, and Pave as the average of the abnormality detection signal P(L) excluding the peak waveform around Lalert, an effective peak height $\Delta P$ is expressed by the equation (6) given below.

$$\Delta P=P(\text{Lalert})-Pave \quad (6)$$

Thereafter, locations LF and LR of both ends of the full width at half maximum of each peak are found.

Figures 15, 16:
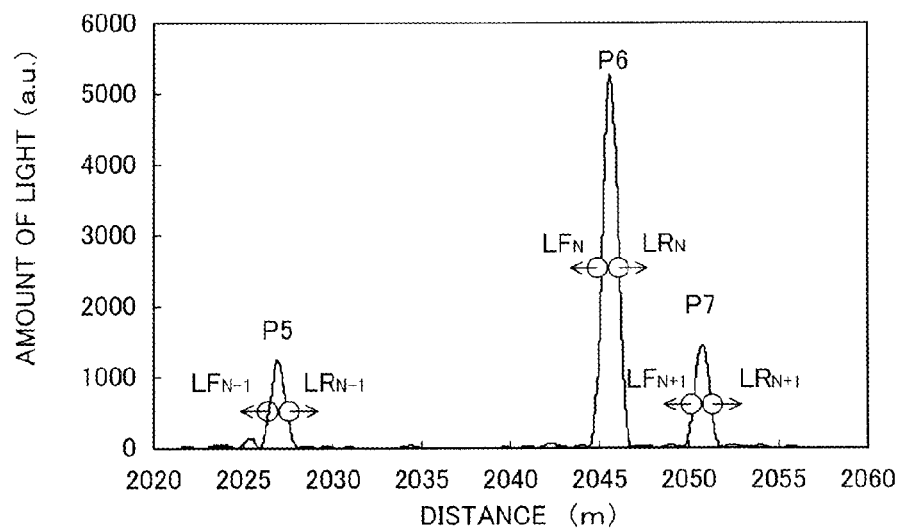
FIG. 15 is a graph describing a second method for calculating transmission loss.
FIG. 16 is a table illustrating an example of the display of transmission losses.

Assume, for example, that as illustrated in FIG. 15, the locations LF and LR of both ends of the full width at half maximum of a peak of interest (P6 in the example of FIG. 15) are $LF_N$ and $LR_N$, respectively, the two locations at both ends of the full width at half maximum of the next peak on the reference location side are $LF_{N-1}$ and $LR_{N-1}$, respectively, and the two locations at both ends of the full width at half maximum of the peak on the opposite side are $LF_{N+1}$ and $LR_{N+1}$, respectively.

The portion of each of the first intensity distribution (NTS1) and the second intensity distribution (NTS2) between $LR_{N-1}$ and $LF_N$ is linearly approximated. Similarly, the portion of each of the first intensity distribution (NTS1) and the second intensity distribution (NTS2) between $LR_N$ and $LF_{N+1}$ is linearly approximated.

The values of the four straight lines thus obtained at the location L (=Lalert) are set as PNTS11(Lalert), PNTS12(Lalert), PNTS21(Lalert), and PNTS22(Lalert), respectively. In this case, a normalized difference $\Delta$PNTS1(Lalert) and a normalized difference $\Delta$PNTS2(Lalert) between the straight lines at the location Lalert are expressed by the equations (7) and (8) given below, respectively.

$$\Delta PNTS1(\text{Lalert})=2 \cdot \text{abs}(PNTS11(\text{Lalert})-PNTS12(\text{Lalert}))/(PNTS11(\text{Lalert})+PNTS12(\text{Lalert})) \quad (7)$$

$$\Delta PNTS2(\text{Lalert})=2 \cdot \text{abs}(PNTS21(\text{Lalert})-PNTS22(\text{Lalert}))/(PNTS21(\text{Lalert})+PNTS22(\text{Lalert})) \quad (8)$$

These values are used in the equation (9) given below to calculate a transmission loss Loss2(L).

$$\text{Loss2}(\text{Lalert})=-10 \cdot \log(1-(\Delta PNTS1(\text{Lalert})+\Delta PNTS2(\text{Lalert}))/2) \quad (9)$$

$LF_N$ and $LP_N$ may be set to locations slightly farther away from the center of the peak than are the locations of the full width at half maximum. This is because, in general, the amount of light in a situation where a loss has occurred exhibits kink characteristics, and the residuals from the approximated linear data may be reduced by excluding regions indicating such kink characteristics.

Proceeding then to step S24, the data processing apparatus 30 determines whether or not the transmission loss Loss2(L) is obtained by the second method. The data processing apparatus 30 proceeds to step S25 if the transmission loss Loss2(L) is obtained by the second method. In step S25, the data processing apparatus 30 compares the transmission loss Loss1(L) obtained by the first method and the transmission loss Loss2(L) obtained by the second method and calculates accuracy A (%) from the equation (10) given below.

$$A = 10^B \times 100 \tag{10}$$

Here, B=(−abs (Loss1(L)−Loss2(L))÷10). Also, the unit of the transmission loss Loss1(L) and the transmission loss Loss2(L) is dB.

Then, the data processing apparatus 30 displays each location where abnormality has occurred, the average of the transmission loss Loss1(L) and the transmission loss Loss2(L), and the accuracy A on a display, for example. FIG. 16 illustrates an example of such display of the transmission losses. In FIG. 16, "Loss by Peak" means the transmission loss Loss1(L) and "Loss by Linear Approximation" means the transmission loss Loss2(L).

On the other hand, if the transmission loss Loss2(L) by the second method is not obtained, the data processing apparatus 30 proceeds to step S26 from step S24. Then, the data processing apparatus 30 displays each location where abnormality has occurred and the transmission loss Loss1(L) on a display, for example.

The abnormality detection system according to this embodiment may accurately detect subtle changes in the stress applied to the optical fiber. Therefore, it is possible to detect the occurrence of abnormality in a facility such as a chemical plant, an oil refinery plant, or a thermal power plant at an early stage, and thus prevent an accident from occurring or worsening.

(Discussion) FIG. 12 is a graph obtained by convoluting the FIR filters in FIGS. 11A and 11B with the first intensity distribution and the second intensity distribution illustrated in FIG. 10, respectively. As compared to the intensity distributions in FIG. 10, the difference between the amounts of light before and after each spot to which a stress is applied is heightened by the convolution of the FIR filters in FIGS. 11A and 11B.

FIG. 13 illustrates the result of calculating the product of the value of FIRNTS1 and the value of FIRNTS2 at each location on the optical fiber in the length direction.

The phase of the noise component included in the first intensity distribution and the phase of the noise component included in the second intensity distribution are not necessarily the same. Then, by calculating the product of the value of FIRNTS1 and the value of FIRNTS2 for each location on the optical fiber in the length direction, the difference between the amounts of light before and after each spot to which the stress is applied is further heightened.

Figure 17A:
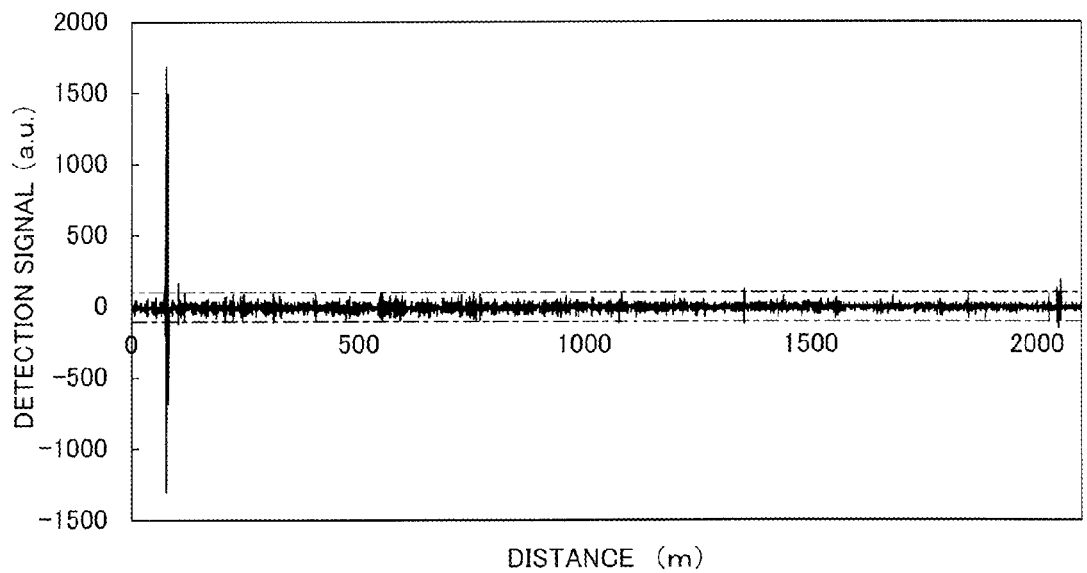
FIG. 17A is a graph illustrating the result of double differentiation on the first intensity distribution NTS1 in FIG. 11.
Figure 17B:
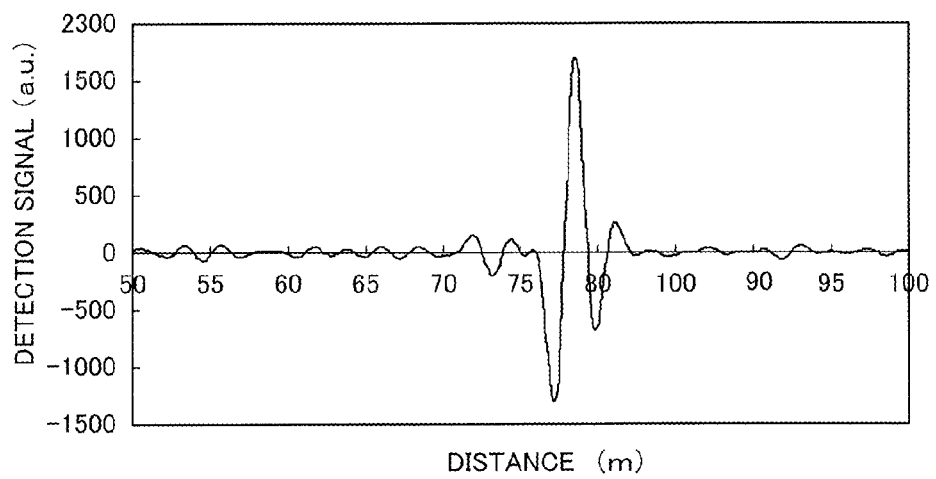
FIG. 17B is a graph illustrating a section of FIG. 17A on a larger scale.

FIG. 17A is a graph illustrating the result of double differentiation on the first intensity distribution NTS1 in FIG. 10. FIG. 17B is a graph illustrating a section of FIG. 17A on a larger scale.

As illustrated in FIGS. 17A and 17B, if the noise level indicated by the dashed lines in FIG. 17A is 3σ, the method involving double differentiation on the intensity distribution may detect one peak which has a large difference from the noise level. On the other hand, as illustrated in FIGS. 13, 14A and 14B, the method disclosed in the embodiment may detect the seven peaks P1 to P7.

Figures 18, 19:
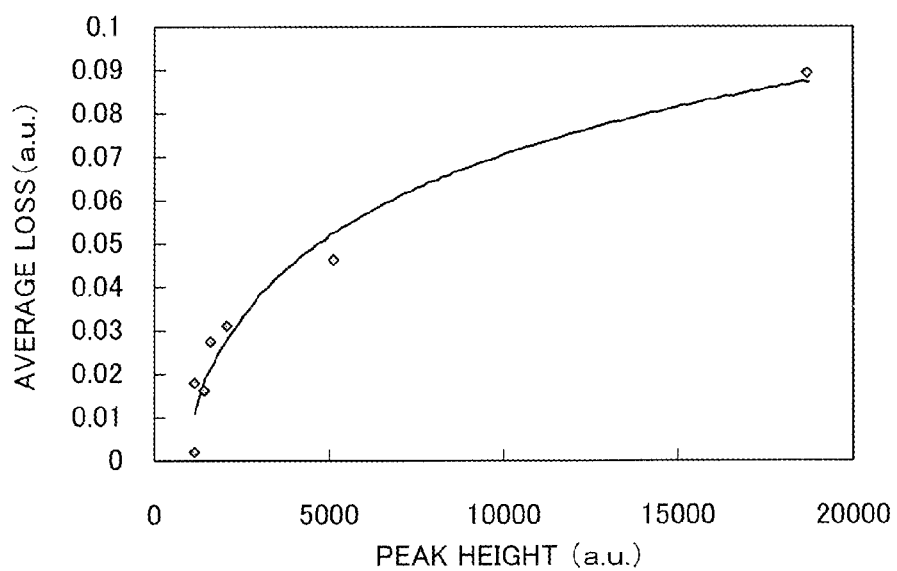
FIG. 18 is a table illustrating the result of finding peak heights (peak values) from FIGS. 13, 14A and 14B.
FIG. 19 is a graph illustrating the relationship between the peak heights and average losses.

FIG. 18 is the result of finding peak heights (peak values) from FIGS. 13, 14A and 14B. Note that the average losses in FIG. 18 are each a value obtained by visually reading the difference in amount of light from the intensity distribution graph and converting the difference into a transmission loss.

With the method involving double differentiation on the intensity distribution of returning light, it is difficult to detect the peak P4 since this peak does not have a large difference from the noise level. On the other hand, with the method according to the embodiment, it is possible to detect the peaks P1 and P7. In other words, with the method according to this embodiment, it is possible to achieve a detection accuracy at least two times higher than that of the method involving double differentiation on the intensity distribution of returning light.

FIG. 19 is a graph illustrating the relationship between peak height and average loss based on FIG. 18. From this FIG. 19, the correction function F (ΔP) may be defined as the equation (11) given below.

$$F(\Delta P) = 0.02694 \cdot \ln(\Delta P) - 0.17762 \tag{11}$$

The correction function F(ΔP) is basically the same for systems which use the same type of optical fiber 26 and the same type of light detection apparatus 20. It is, however, preferably to find a correction function F(ΔP) in advance via tests if the type of optical fiber 26 and the type of light detection apparatus 20 are not the same.

The correction function F(ΔP) includes ln(ΔP) for the following reason. Specifically, when Pow1 is the amount of light at a given location in the optical fiber in the length direction, Pow2, which is the amount of light at a location away from that given location by L, is expressed as Pow2=Pow1·exp(−α·L), where α is a loss coefficient. Thus, the loss coefficient α is α=(ln(Pow1÷Pow2))÷L. Since the correction function F(ΔP) is related to the loss coefficient α, the correction function F(ΔP) includes ln(ΔP).

FIG. 20 illustrates the result of finding average losses (unit: dB) by using this correction function F(ΔP). In this FIG. 20, no large difference is observed between the transmission losses found from the peak values by using the method disclosed in this embodiment and the transmission losses read visually from the intensity distribution of returning light. This demonstrates that the transmission losses found by the method disclosed in the embodiment are reliable.

The second method described above will be described below in greater detail.

Assume, for example, that locations situated outward of the peak center by 1 m are employed as LF and LR, respectively. FIG. 21 illustrates the locations of the full width at half maximum (the location of the left half of the full width at half maximum and the location of the right half of the full width at half maximum) of each of the peaks P4 to P7 in the length direction of the optical fiber and the locations LF and LR.

Figures 22, 23:
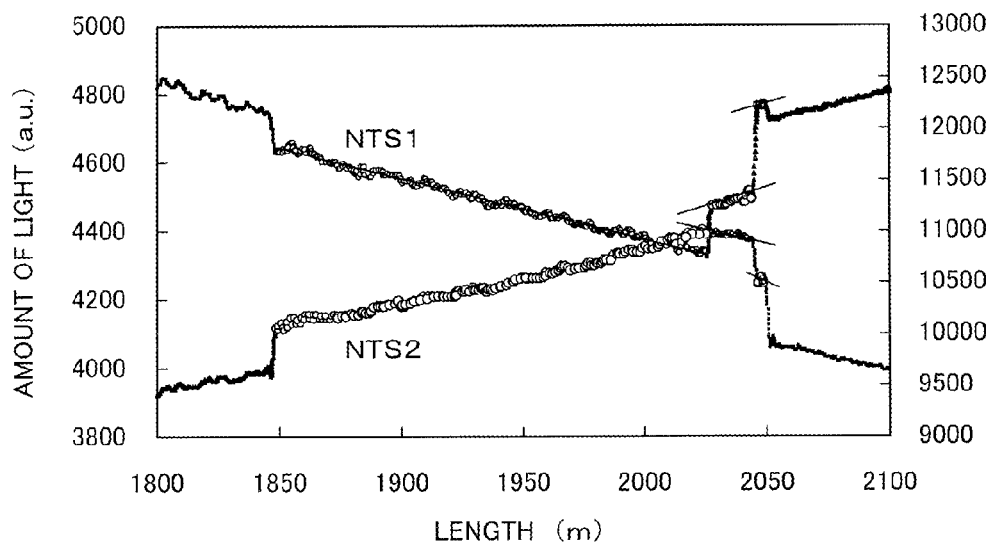
FIG. 22 is a graph illustrating linear approximation of the first intensity distribution NTS1 and the second intensity distribution NTS2.
FIG. 23 is a table illustrating the result of finding the transmission losses (losses by linear approximation) at the locations of the peaks P5 and P6.

Here, as illustrated in FIG. 22, focusing on the peak P5, each of a portion to the left of LF, a portion to the right of LR, and a portion between LF and LR is linearly approximated for each of the first intensity distribution NTS1 and the second intensity distribution NTS2 by the least squares method, the least-median-of-squares (LMedS) method, or the like. Then, from these straight lines, the differences between the amounts of light at the location of P5 are determined, and the transfer loss is calculated. Similarly, focusing on the peak P6, each of a portion to the left of LF, a portion to the right of LR, and a portion between LF and LR is linearly approximated by the least squares method, the least-median-of-squares (LMedS) method, or the like, the differences between the amounts of light at the location of P6 are determined, and the transfer loss is calculated.

FIG. 23 illustrates the result of finding the transmission losses (losses by linear approximation) at the locations of the peaks P5 and P6 as described above. Moreover, FIG. 23 illustrates the average losses visually read from the intensity distribution of returning light (see FIG. 20) as well.

As is clear from this FIG. 23, the average losses visually read from the intensity distribution of returning light and the transmission losses obtained by the second method substantially coincide with each other.

The applicability of the technique disclosed above will be described below.

Figure 24:
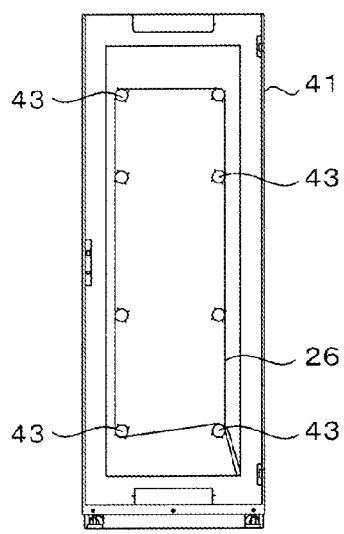
FIG. 24 is a view illustrating applicability 1.

(Applicability 1) FIG. 24 illustrates an example of application to a system configured to detect abnormality in how an optical fiber is laid on a server rack of a data center to manage air conditioning.

When a server rack 41 is newly installed in a data center, an optical fiber 26 is drawn out from an optical fiber cassette (not illustrated) placed under the floor, and the optical fiber 26 is laid on the server rack 41 with jigs 43.

Even if the operator thinks that he or she properly laid the optical fiber 26, the optical fiber 26 may be wound improperly on some of the jigs 43, thereby causing decrease in transmission loss. The decrease in transmission loss leads not only to the problem of decrease in temperature detection accuracy as described above but also to decrease in the life of the optical fiber 26.

By using the technique disclosed in the embodiment, however, the decrease in transmission loss due to the improper winding on the jigs 43 may be detected in real time. Such information is notified to the manager, and the manager notifies the improperly laid locations and a correcting instruction to the operator. In this way, the optical fiber 26 may be properly re-laid.

(Applicability 2) FIGS. 25A to 25D illustrate an example where the abnormality detection system described in the embodiment is applied to the detection of abnormality at a connected portion of pipes as illustrated in FIG. 1.

Figure 25A:
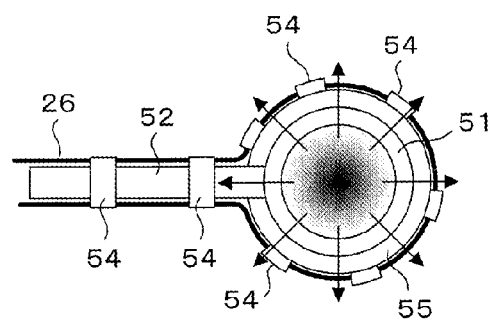
FIGS. 25A to 25D are views illustrating applicability 2.

Assume that while a plant is operated, high-temperature liquid or gas flows inside a main pipe 51, as illustrated in FIG. 25A. In this case, the pipe 51 expands when the plant is operated, and the pipe 51 shrinks when the plant is stopped. The amount of transmission loss in the optical fiber 26 when the plant is operated and the amount of transmission loss when the plant is stopped are stored in advance in the data processing apparatus 30.

Note that in FIGS. 25A to 25D, reference numeral 54 denotes pieces of tape fixing the optical fiber 26, and reference numeral 55 denotes a heat insulation material and a protection pipe disposed around the main pipe 51.

Figure 25C:
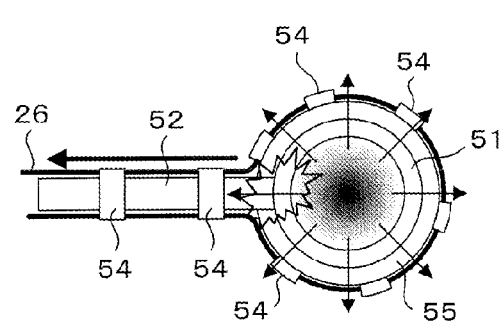
Figure 25B:
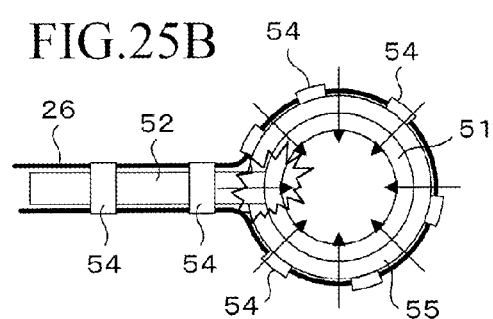
Figure 25D:
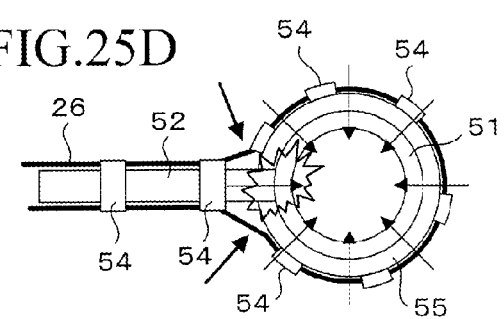

Metal fatigue occurs at a welded portion of the main pipe 51 and a branch pipe 52 as illustrated in FIG. 25B when the plant is stopped, for example. In this case, the next time the plant is run, the branch pipe 52 is pushed farther outwardly than usual as illustrated in FIG. 25C. When the plant then shifts to the stopped state, the branch pipe 52 thus pushed does not fully return as illustrated in FIG. 25D, thereby pulling the optical fiber 26. As a result, the abnormality detection system detects the abnormality.

By detecting abnormality at a connected portion of pipes in a plant or the like as described above, a serious accident is prevented from occurring.

Figure 26:
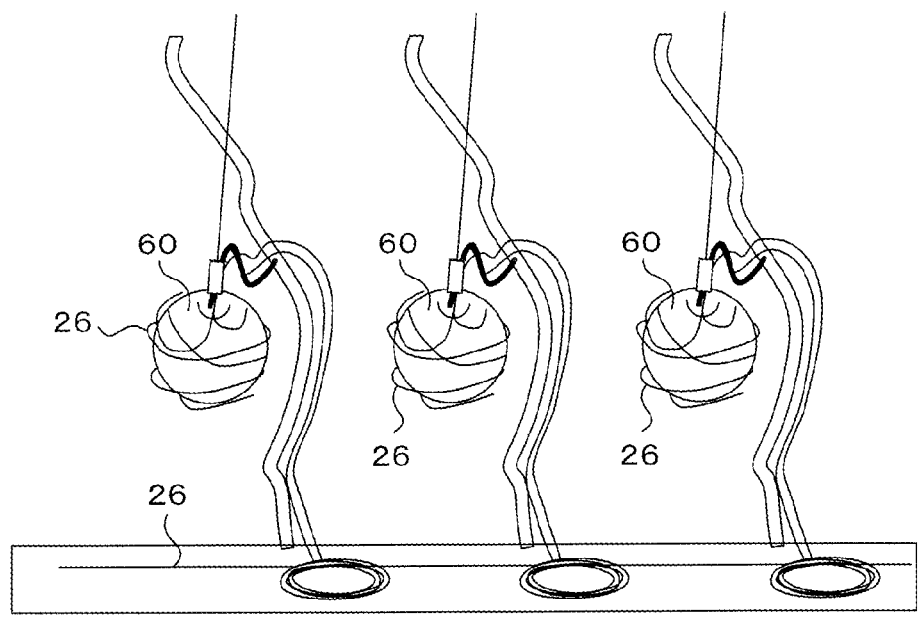
FIG. 26 is a view illustrating applicability 3.

(Applicability 3) FIG. 26 illustrates an example where the abnormality detection system described in the embodiment is applied to the growing of expensive fruits in a greenhouse and to the protection against theft thereof.

In this example, assume that, for the growing of Crown Melon in a greenhouse, a temperature distribution measurement apparatus (DTS) is used to measure the temperature of the soil, the temperature of the ambient air, and the temperature of the fruit, and the temperature of the inside of the greenhouse is managed based on these measurement results. Moreover, in this example, assume that the temperature distribution measurement apparatus is used also as the light detection apparatus 20 in FIG. 7, and is connected to the data processing apparatus 30 to be used for abnormality detection as well.

When a thief steals a melon 60, for example, the thief tries to unwind an optical fiber 26 wound around the melon 60. By acting carefully, the thief may avoid cutting the optical fiber 26. However, a subtle transmission loss inevitably occurs when the thief tries to unwind the optical fiber 26. Thus, the abnormality detection system may detect the abnormality.

Upon detection of the abnormality, the abnormality detection system turns on an alarm lamp or actuates an alarm buzzer as well as notifies the occurrence of the abnormality to the manager. In this way, it is possible to prevent immense damage.

All examples and conditional language recited herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An abnormality detection system comprising:
an optical fiber;
a backscattered light detection unit connected to one end and another end of the optical fiber and configured to acquire a first intensity distribution of backscattered light by causing light to enter the optical fiber from the one end, and to acquire a second intensity distribution of backscattered light by causing light to enter the optical fiber from the other end; and
a data processing unit configured to calculate a product of a value obtained by applying a first FIR (Finite Impulse Response) filter to the first intensity distribution acquired by the backscattered light detection unit, and a value obtained by applying a second FIR filter to the second intensity distribution acquired by the backscattered light detection unit, for each of locations on the optical fiber in a length direction of the optical fiber, and to determine whether or not abnormality is present based on a result of the calculation.

2. The abnormality detection system according to claim 1, wherein the first FIR filter and the second FIR filter each have characteristics of both a differential filter and a low-pass filter.

3. The abnormality detection system according to claim 2, wherein characteristics of the first FIR filter and characteristics of the second FIR filter are symmetric with each other in positive-negative directions.

4. The abnormality detection system according to claim 2, wherein the second FIR filter has same characteristics as the first FIR filter.

5. The abnormality detection system according to claim 1, wherein the data processing unit calculates the product of the value obtained by applying the first FIR filter to the first intensity distribution and the value obtained by applying the second FIR filter to the second intensity distribution, and calculates a location at which abnormality has occurred and a transmission loss at the location from a peak in a graph obtained by the calculation of the product.

6. The abnormality detection system according to claim 5, wherein the transmission loss is capable of being expressed with a function $F(\Delta P)$, where $\Delta P$ is a height of the peak in the graph, and the data processing unit calculates a transmission loss $Loss1(L)$ at a location L of the peak in decibel by using $Loss1(L)=-10 \cdot \log(1-F(\Delta P))$.

7. The abnormality detection system according to claim 5, wherein the data processing unit linearly approximates each of portions of the first intensity distribution before and after the peak and each of portions of the second intensity distribution before and after the peak and calculates the transmission loss from amounts of change in amounts of the backscattered light at a location of the peak.

8. The abnormality detection system according to claim 1, wherein the backscattered light detection unit is capable of acquiring a temperature distribution in the length direction of the optical fiber by detecting Raman scattered light.

9. The abnormality detection system according to claim 1, wherein the optical fiber is laid along a pipe.

10. The abnormality detection system according to claim 1, wherein the optical fiber is laid on electronic equipment.

11. The abnormality detection system according to claim 1, wherein the optical fiber is laid around a plant.

12. An abnormality detection method comprising:

by using a backscattered light detection unit, acquiring a first intensity distribution of backscattered light by causing light to enter an optical fiber from one end of the optical fiber, and, by using the backscattered light detection unit, acquiring a second intensity distribution of backscattered light by causing light to enter the optical fiber from another end of the optical fiber; and by using a data processing unit, calculating a product of a value obtained by applying a first FIR (Finite Impulse Response) filter to the first intensity distribution, and a value obtained by applying a second FIR filter to the second intensity distribution for each of locations on the optical fiber in a length direction of the optical fiber.

13. The abnormality detection method according to claim 12, wherein the first FIR filter and the second FIR filter each have characteristics of both a differential filter and a low-pass filter.

14. The abnormality detection method according to claim 13, wherein characteristics of the first FIR filter and characteristics of the second FIR filter are symmetric with each other in positive-negative directions.

15. The abnormality detection method according to claim 13, wherein the second FIR filter has same characteristics as the first FIR filter.

16. The abnormality detection method according to claim 12, wherein the data processing unit calculates the product of the value obtained by applying the first FIR filter to the first intensity distribution and the value obtained by applying the second FIR filter to the second intensity distribution, and calculates a location at which abnormality has occurred and a transmission loss at the location from a peak in a graph obtained by the calculation of the product.

17. The abnormality detection method according to claim 16, wherein the transmission loss is capable of being expressed with a function $F(\Delta P)$, where $\Delta P$ is a height of the peak in the graph, and the data processing unit calculates a transmission loss $Loss1(L)$ at a location L of the peak in decibel by using $Loss1(L)=-10 \cdot \log(1-F(\Delta P))$.

18. The abnormality detection method according to claim 16, wherein the data processing unit linearly approximates each of portions of the first intensity distribution before and after the peak and each of portions of the second intensity distribution before and after the peak and calculates the transmission loss from amounts of change in amounts of the backscattered light at a location of the peak.

19. The abnormality detection method according to claim 12, wherein, even when a location is present where a value of the product of the value obtained by applying the first FIR filter to the first intensity distribution and the value obtained by applying the second FIR filter to the second intensity distribution is above a set value, the data processing unit determines that no abnormality is present at the location when the location is where a transmission loss is expected in advance.

20. The abnormality detection method according to claim 12, wherein a temperature distribution measurement apparatus is used as the backscattered light detection unit.

* * * * *